US008882671B2

(12) United States Patent
Sasaki et al.

(10) Patent No.: US 8,882,671 B2
(45) Date of Patent: Nov. 11, 2014

(54) ULTRASONIC DIAGNOSTIC DEVICE, ULTRASONIC IMAGE PROCESSING APPARATUS, ULTRASONIC IMAGE ACQUIRING METHOD AND ULTRASONIC DIAGNOSIS DISPLAY METHOD

(75) Inventors: Takuya Sasaki, Nasu-gun (JP); Kenji Hamada, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1123 days.

(21) Appl. No.: 12/579,541

(22) Filed: Oct. 15, 2009

(65) Prior Publication Data

US 2010/0099987 A1    Apr. 22, 2010

(30) Foreign Application Priority Data

Oct. 16, 2008   (JP) .................................. 2008-267614

(51) Int. Cl.
*A61B 8/00*      (2006.01)
*G01S 7/52*      (2006.01)
*A61B 8/14*      (2006.01)
*A61B 8/08*      (2006.01)

(52) U.S. Cl.
CPC ............... *A61B 8/14* (2013.01); *G01S 7/52073* (2013.01); *A61B 8/4461* (2013.01); *G01S 7/52098* (2013.01); *A61B 8/523* (2013.01); *G01S 7/52074* (2013.01); *G01S 7/52085* (2013.01)
USPC ........... 600/437; 600/443; 600/444; 600/450; 600/459; 600/407

(58) Field of Classification Search
USPC .................. 600/407, 437, 443, 444, 450, 459
See application file for complete search history.

(56) References Cited

U.S. PATENT DOCUMENTS 5,655,535 A *   8/1997   Friemel et al. ................ 600/443
6,966,878 B2   11/2005   Schoisswohl et al.

(Continued)

FOREIGN PATENT DOCUMENTS

JP          7-328007       12/1995
JP       2005-152346 A      6/2005

(Continued)

OTHER PUBLICATIONS

Office Action issued Jun. 24, 2011 in Chinese Patent Application No. 200910205165.1 (with English translation).
Office Action issued Sep. 24, 2013 in Japanese Patent Application No. 2009-238473 (with English language translation).

*Primary Examiner* — Joel Lamprecht
(74) *Attorney, Agent, or Firm* — Oblon, Spivak, McClelland, Maier & Neustadt, L.L.P.

(57) ABSTRACT

Volume data are collected by swing scanning in which frames in different field angle settings are mixed by a wide scan set at a wide field angle to image a diagnostic target and an index part for recognizing the position of the diagnostic target and by a narrow scan set at a field angle θ2 narrower than the field angle in the wide scan to image the diagnostic target with high time resolution. Then, the wide ultrasonic image is used to set spatial coordinates based on the index part. The spatial coordinates are used to align the narrow ultrasonic image. While this positional relation is being maintained, the wide ultrasonic image, the narrow ultrasonic image and a given ultrasonic image are displayed in a predetermined form.

19 Claims, 11 Drawing Sheets

(56) References Cited

U.S. PATENT DOCUMENTS

| | | |
|---|---|---|
| 6,980,844 B2 | 12/2005 | Schoisswohl |
| 7,744,534 B2 * | 6/2010 | Chalana et al. ............... 600/437 |
| 2005/0251036 A1 * | 11/2005 | Abuhamad ................... 600/437 |
| 2006/0241457 A1 * | 10/2006 | Nadadur et al. ............. 600/450 |

FOREIGN PATENT DOCUMENTS

| | | |
|---|---|---|
| JP | 2005-349215 A | 12/2005 |
| JP | 2006-218089 A | 8/2006 |
| JP | 2008-534082 A | 8/2008 |

\* cited by examiner

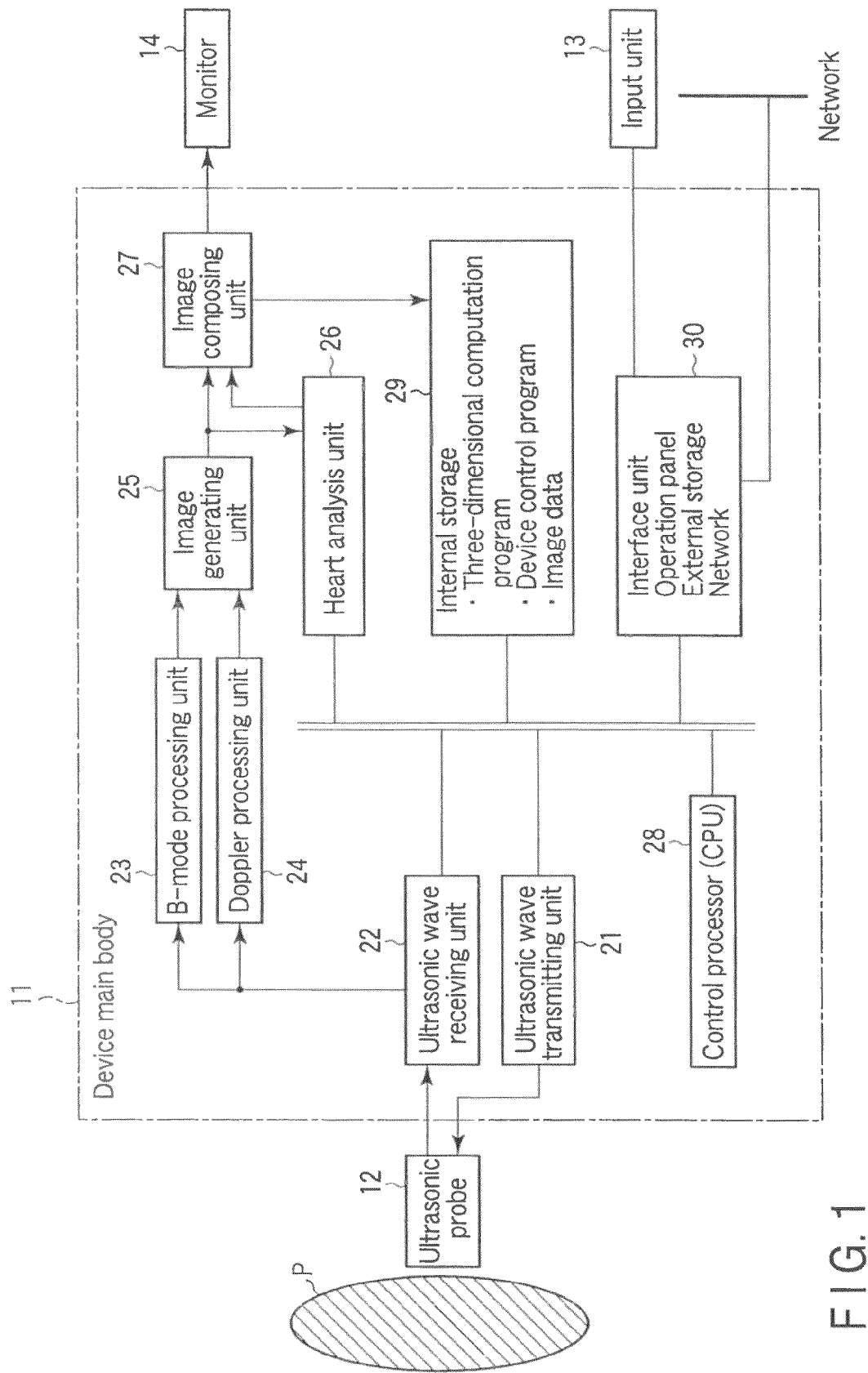
F I G. 1

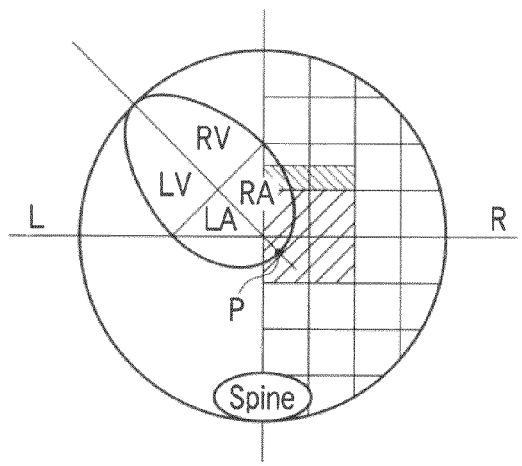
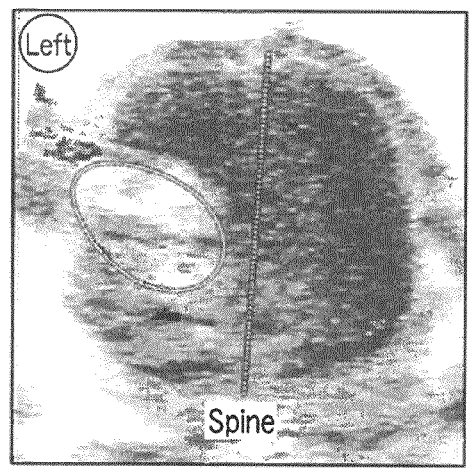
F I G. 6A    F I G. 6B
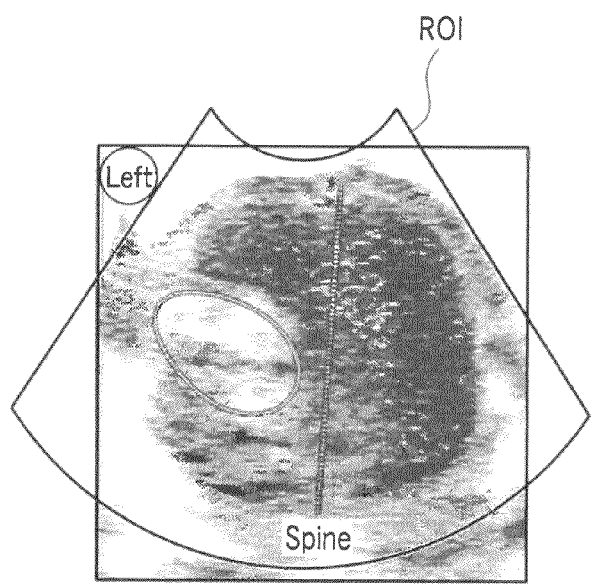
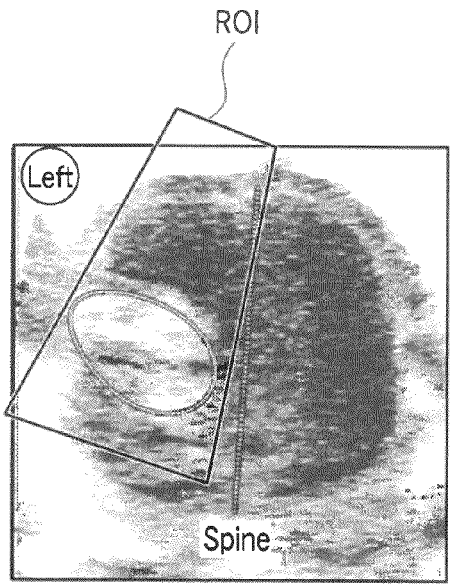
F I G. 7A    F I G. 7B

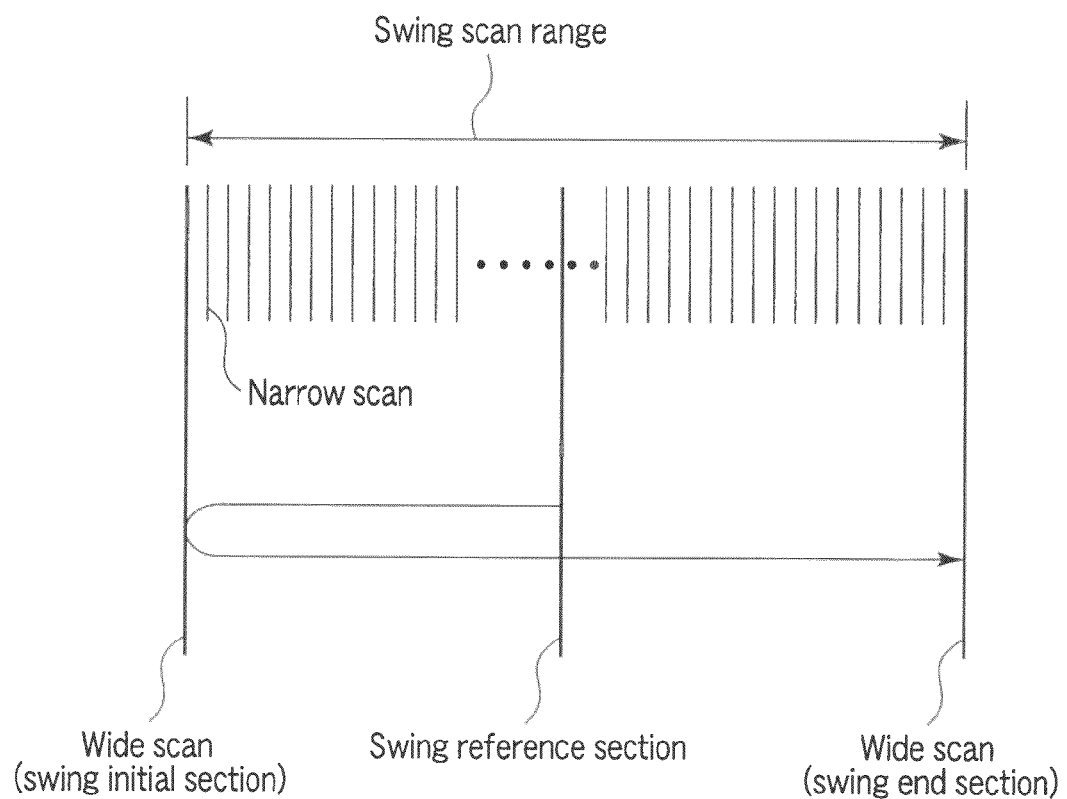
F I G. 10
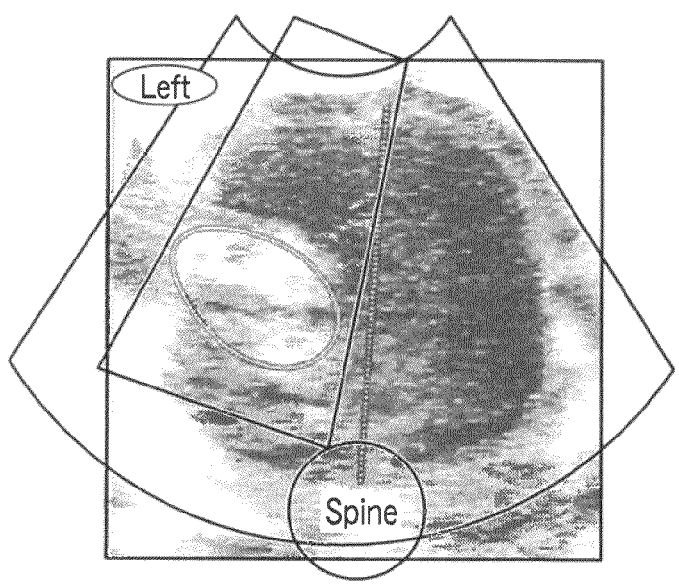
F I G. 11

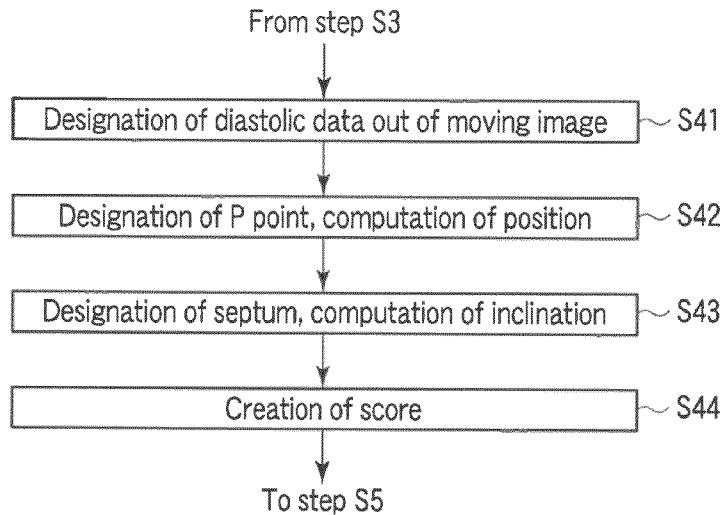
FIG. 14
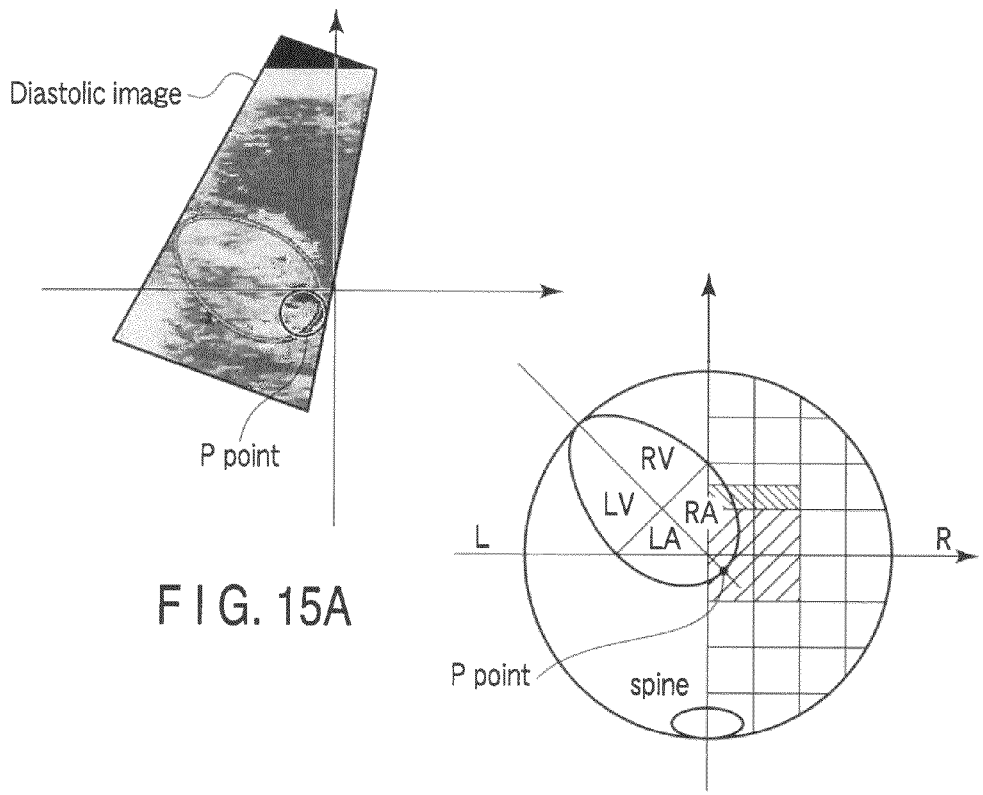
FIG. 15A
FIG. 15B

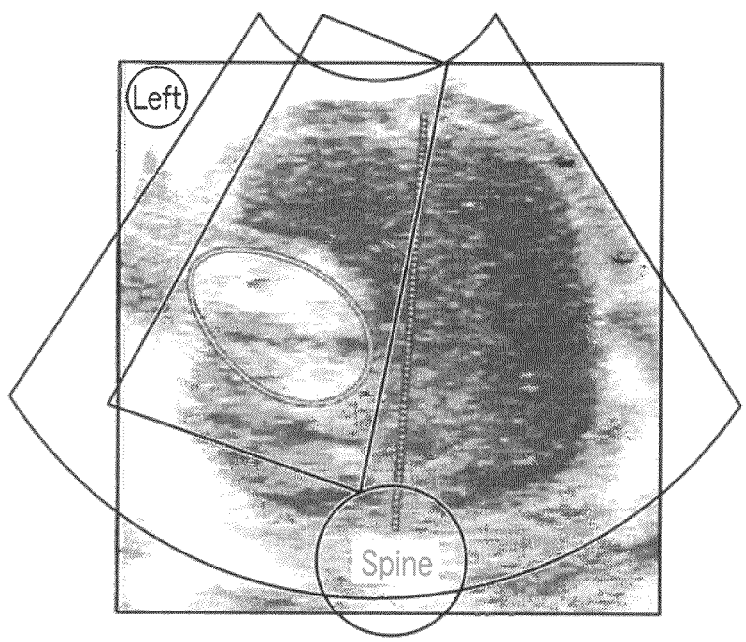
F I G. 18A
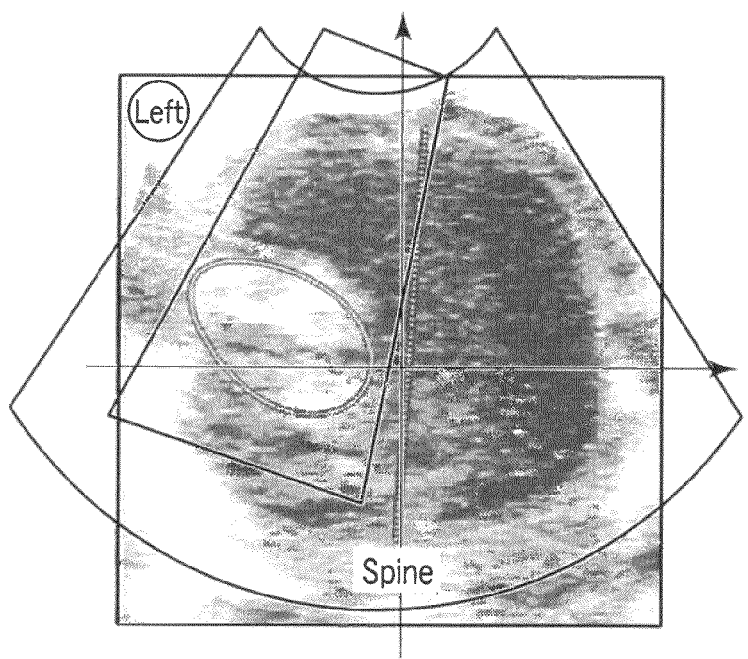
F I G. 18B

ULTRASONIC DIAGNOSTIC DEVICE, ULTRASONIC IMAGE PROCESSING APPARATUS, ULTRASONIC IMAGE ACQUIRING METHOD AND ULTRASONIC DIAGNOSIS DISPLAY METHOD

CROSS-REFERENCE TO RELATED APPLICATIONS

This application is based upon and claims the benefit of priority from prior Japanese Patent Application No. 2008-267614, filed Oct. 16, 2008, the entire contents of which are incorporated herein by reference.

BACKGROUND OF THE INVENTION

1. Field of the Invention

The present invention relates to an ultrasonic diagnostic apparatus, an ultrasonic image processing apparatus, an ultrasonic image acquiring method and an ultrasonic diagnosis display method capable of volume scanning using, for example, a spatio-temporal imaging correlation (STIC) function.

2. Description of the Related Art

An ultrasonic diagnosis enables the beating of the heart or the motion of a fetus to be obtained in real-time display by a simple operation of applying an ultrasonic probe onto the body surface. Moreover, the ultrasonic diagnosis is highly safe. Therefore, the ultrasonic diagnosis enables repeated examinations. The ultrasonic diagnosis can also be said to be a convenient diagnostic technique in that its system is smaller in scale than, for example, other X-ray, CT and MRI diagnostic instruments and can be easily moved to a bedside for an examination. An ultrasonic diagnostic apparatus used in this ultrasonic diagnosis varies depending on the kind of its function. Meanwhile, ultrasonic diagnostic apparatus that are small enough to carry with one hand have been developed. The ultrasonic diagnosis has no effect of radiation exposure in contrast with X-rays, and can be used in, for example, an obstetrical service or a home health care service.

Furthermore, in recent years, the ultrasonic diagnostic apparatus can be used to acquire volume data and observe a three-dimensional moving image in real time. One of the functions used to perform such a three-dimensional moving image diagnosis is an STIC function. According to this function, frame data are collected without referring to an electrocardiogram (ECG), and volume data is constructed by a frequency analysis of the collected frame data. Thus, an obstetrician, a gynecologist or a circulatory organ doctor can anatomically diagnose the motion of the heart of a fetus. When a heart disease of a fetus is diagnosed using the ultrasonic diagnostic apparatus, it is difficult to refer to an ECG signal of the fetus, so that the use of the STIC function is indispensable.

However, even when the STIC function is used, a volume scan with a wide field angle including a spine as a mark is necessary in order to recognize the position of the heart in the chest of the fetus. Performing the volume scan with a wide field angle leads to a decrease in volume rate, which can not be said to be preferable in terms of the analysis of the motion of the heart.

BRIEF SUMMARY OF THE INVENTION

The present invention has been made in view of the above-described circumstances. It is an object of the present invention to provide an ultrasonic diagnostic apparatus, an ultrasonic image processing apparatus, an ultrasonic image acquiring method and an ultrasonic diagnosis display method, wherein even a volume scan with a wide field angle including a spine as a mark for recognizing the position of the heart can be performed such that the position of the heart in the chest of a fetus can be accurately recognized.

According to an aspect of the present invention, there is provided an ultrasonic diagnostic apparatus including: an ultrasonic scan unit which acquires ultrasonic image data by performing a first ultrasonic scan and a second ultrasonic scan in a scan plane set in a subject, the first ultrasonic scan using a first field angle set to a size including a diagnostic target and a part serving as an index to recognize a position of the diagnostic target and the second ultrasonic scan including the diagnostic target in the subject; a control unit which controls the ultrasonic scan unit so that a plurality of ultrasonic image data sets regarding the diagnostic target are acquired by performing at least one second ultrasonic scan and a plurality of first ultrasonic scans; and a setting unit which sets, in the ultrasonic image data, a coordinate axis based on the index part by use of at least one of second ultrasonic images obtained by the second ultrasonic scan.

According to another aspect of the present invention, there is provided an ultrasonic image processing apparatus including: a storage unit which stores a plurality of ultrasonic image data sets, the ultrasonic image data being acquired by performing a first ultrasonic scan and a second ultrasonic scan in a scan plane set in a subject, the first ultrasonic scan using a first field angle set to a size including a diagnostic target and a part serving as an index to recognize a position of the diagnostic target and the second ultrasonic scan using a second field angle set to a size including the diagnostic target in the subject; and a setting unit which sets, in the plurality of ultrasonic image data sets, a coordinate axis based on the index part by use of at least one of second ultrasonic images obtained by the second ultrasonic scan.

According to yet another aspect of the present invention, there is provided an ultrasonic image acquiring method including: acquiring a plurality of ultrasonic image data sets regarding a diagnostic target by performing a first ultrasonic scan and a second ultrasonic scan in a scan plane set in a subject, the first ultrasonic scan using a first field angle set to a size including a diagnostic target and a part serving as an index to recognize the position of the diagnostic target and the second ultrasonic scan using a second field angle set to a size including the diagnostic target in the subject; and a setting unit which sets, in the ultrasonic image data, a coordinate axis based on the index part by use of at least one of second ultrasonic images obtained by the second ultrasonic scan.

According to yet another aspect of the present invention, there is provided an ultrasonic image display method including: setting a coordinate axis based on an index part in a plurality of ultrasonic image data sets, the plurality of ultrasonic image data sets being obtained by performing a first ultrasonic scan and a second ultrasonic scan in a scan plane set in a subject, the first ultrasonic scan using a first field angle set to a size including a diagnostic target and a part serving as an index to recognize the position of the diagnostic target and the second ultrasonic scan using a second field angle set to a size including the diagnostic target in the subject; and displaying a superposed image on which at least two of the coordinate axis, a position according to the coordinate axis, the first ultrasonic image, a second ultrasonic image acquired by the second ultrasonic scan, and an ultrasonic image corresponding to a given section set in the plurality of ultrasonic image data sets are superposed.

BRIEF DESCRIPTION OF THE SEVERAL VIEWS OF THE DRAWING

FIG. 1 shows a block configuration diagram of an ultrasonic diagnostic apparatus 1 according to the present embodiment;

FIGS. 6A and 6B are diagrams for explaining the swing reference section setting in the case where the heart of the fetus is targeted for a diagnosis;

FIGS. 7A and 7B are diagrams for explaining ROI setting for a wide scan and a narrow scan on a swing reference section;

FIG. 10 is a diagram for explaining the scan sequence in step S2;

FIG. 11 is a diagram illustrating the state of a spine position designated on a wide ultrasonic image;

FIG. 14 is a flowchart showing the flow of computing a P point of the heart, etc. according to step S4;

FIGS. 15A and 15B are diagrams for explaining the designation of the P point of the heart and the computation of a position;

FIGS. 18A and 18B are diagrams showing one example of the display form of the wide ultrasonic image and the narrow ultrasonic image acquired by the heart analysis function.

DETAILED DESCRIPTION OF THE INVENTION

Figure 2:
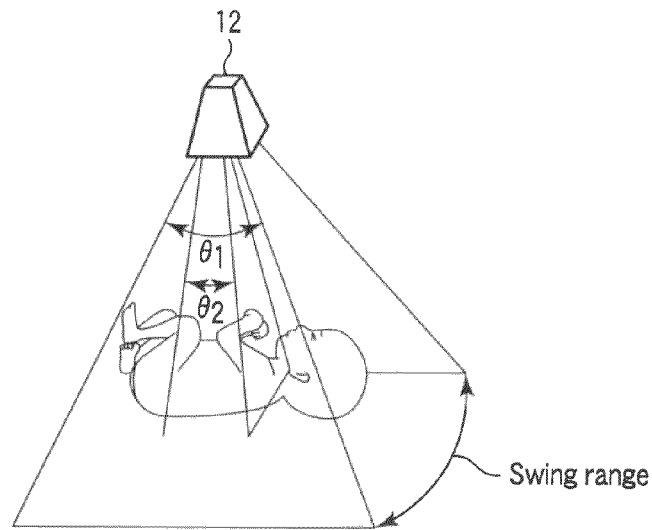
FIG. 2 is a diagram showing one example of a volume scan performed by processing using a heart analysis function.

An embodiment of the present invention will hereinafter be described with reference to the drawings. It is to be noted that components having about the same functions and configurations in the following description are provided with the same reference numbers and are repeatedly explained only when necessary.

FIG. 1 shows a block configuration diagram of an ultrasonic diagnostic apparatus 1 according to the present embodiment. As shown, the present ultrasonic diagnostic apparatus 1 includes an ultrasonic probe 12, an input unit 13, a monitor 14, an ultrasonic wave transmitting unit 21, an ultrasonic wave receiving unit 22, a B-mode processing unit 23, a Doppler processing unit 24, an image generating unit 25, an image memory 26, an image composing unit 27, a control processor (CPU) 28, an internal storage 29, an interface unit 30 and an image processing unit 31. Functions of the respective components are described below.

The ultrasonic probe 12 has a plurality of piezoelectric vibrators for generating ultrasonic waves on the basis of a drive signal from the ultrasonic wave transmitting unit 21 and converting reflected waves from a subject into an electric signal, matching layers provided in the piezoelectric vibrators, a backing member for preventing rearward propagation of the ultrasonic waves from the ultrasonic probe 12, etc. When the ultrasonic waves are transmitted from the ultrasonic probe 12 to a subject P, the transmitted ultrasonic waves are successively reflected by a discontinuous plane of acoustic impedance in a body tissue, and received by the ultrasonic probe 12 as an echo signal. The amplitude of the echo signal depends on the difference of the acoustic impedance in the discontinuous plane where the ultrasonic waves are reflected. Moreover, an echo in the case where the transmitted ultrasonic pulse is reflected by a moving blood flow or the surface of, for example, a heart wall is subjected to a frequency shift so that a velocity component of the moving object in the ultrasonic wave transmitting direction depends on a Doppler effect.

In addition, the ultrasonic probe 12 provided in the present ultrasonic diagnostic apparatus is capable of ultrasonically scanning the three-dimensional region of a subject. Thus, the ultrasonic probe 12 has, for example, a configuration for mechanically swinging the vibrators along a direction perpendicular to their arrangement direction and ultrasonically scanning the three-dimensional region, and a configuration for ultrasonically scanning the three-dimensional region under electric control using two-dimensionally arranged two-dimensional vibrating elements. When the former configuration is used, the three-dimensional scan of the subject is performed by a swing circuit (swing mechanism). Therefore, a person who performs an examination can automatically acquire a plurality of two-dimensional tomograms simply by putting the main body of the probe into contact with the subject. An accurate distance between sections can also be detected from the controlled swing velocity. When the latter configuration is used, the three-dimensional region can be, in principle, ultrasonically scanned in a time equal to the time needed to acquire conventional two-dimensional tomograms. In the present embodiment, for a more specific explanation, the ultrasonic probe 12 ultrasonically scans the three-dimensional region by mechanical swinging.

The input unit 13 has various switches, a button, a track ball, a mouse, a keyboard, etc. which are connected to a device main body 11 and which take, into the device main body 11, various instructions from an operator, conditions, an instruction to set a region of interest (ROI), and an instruction to set various image quality conditions. For example, if the operator operates an end button or a FREEZE button of the input unit 13, the transmission and reception of the ultrasonic waves are finished, and the ultrasonic diagnostic apparatus is temporarily stopped.

The monitor 14 displays, in a given format, morphologic information (a normal B-mode image) regarding the inside of a body, blood flow information (an average velocity image, a dispersed image, a power image, etc.), a wide ultrasonic image, a narrow ultrasonic image, a given section ultrasonic image, etc., on the basis of a video signal from the scan converter 25.

The ultrasonic wave transmitting unit 21 has an unshown trigger generating circuit, a delay circuit and a pulser circuit. The pulser circuit repeatedly generates, at a predetermined rate frequency fr Hz (period; 1/fr seconds), a rate pulse for forming transmission ultrasonic waves. In the delay circuit, a delay time necessary to converge the ultrasonic waves into the shape of a beam for each channel and to determine transmission directional characteristics is provided to each rate pulse. The trigger generating circuit applies a drive pulse to the ultrasonic probe 12 by the timing based on the rate pulse.

In addition, the ultrasonic wave transmitting unit 21 has a function to enable a transmission frequency, a transmission drive voltage, etc. to be instantaneously changed to perform a predetermined scan sequence in accordance with the instruction from the control processor 28. In particular, the transmission drive voltage is changed by a linear amplifier type transmitting circuit capable of instantaneously changing its value or by a mechanism which electrically switches a plurality of power units.

The ultrasonic wave receiving unit 22 has an amplifier circuit, an A/D converter, an adder, etc. that are not shown. The amplifier circuit amplifies, for each channel, the echo signal taken in via the probe 12. The A/D converter provides the amplified echo signal with a delay time necessary to determine reception directional characteristics before addition in the adder. A reflection component from a direction corresponding to the reception directional characteristics of the echo signal is emphasized by the addition, and a synthetic beam of the ultrasonic wave transmission and reception is formed by the reception directional characteristics and the transmission directional characteristics.

The B-mode processing unit 23 receives the echo signal from the transmitting/receiving unit 21, subjects the received echo signal to logarithmic amplification, envelope detecting processing, etc., and generates data in which signal intensity is represented by luminance. This data is transmitted to the scan converter 25, and displayed on the monitor 14 as a B-mode image in which the intensity of the reflected waves is represented by luminance.

The Doppler processing unit 24 performs a frequency analysis of velocity information in accordance with the echo signal received from the transmitting/receiving unit 21, extracts a blood flow and tissues attributed to the Doppler effect and contrast media components, and obtains the blood flow information including, for example, an average velocity, dispersion and power for multiple points.

The image generating unit 25 generally converts (scan-converts) a scan line signal sequence of the ultrasonic scan into a scan line signal sequence in a general video format typified by television, and generates an ultrasonic diagnostic image as a display image.

The heart analysis processing unit 26 enables a later-described heart analysis function using a plurality of volume data collected by different field angle settings. The operation of this heart analysis processing unit 26 will be described later in detail.

The image composing unit 27 combines an image received from the image generating unit 25 or the heart analysis processing unit 26 with character information, a scale or the like of various parameters, and outputs the result to the monitor 14 as a video signal.

The control processor 28 has a function as an information processing apparatus (computer), and controls the operation of the main body of the present ultrasonic diagnostic apparatus. The control processor 28 reads an exclusive program for enabling the heart analysis function and a control program for performing a predetermined scan sequence from the internal storage 29. Then, the control processor 28 expands the read programs on its memory, and performs computations and control associated with various kinds of processing.

The internal storage 29 stores a predetermined scan sequence for collecting a plurality of volume data by different field angle settings, the exclusive program for enabling the later-described heart analysis function, a control program for performing image generation and display processing, diagnostic information (e.g., patient IDs and doctor's observations), diagnostic protocols, transmission/reception conditions, a body mark generating program and other data groups. The internal storage 29 is also used to store images in the image memory 26 if necessary. The data in the internal storage 29 can also be transferred to an external peripheral device via the interface unit 30.

The interface unit 30 is an interface associated with the input unit 13, a network and a new external storage (not shown). Data on the ultrasonic image and analytic results obtained by this device, for example, can be transferred to another device by the interface unit 30 via the network.

(Heart Analysis Function)

Next, the heart analysis function of the present ultrasonic diagnostic apparatus 1 is explained. This function allows the volume data to be collected by swing scanning in which frames in different field angle settings are mixed by a wide scan set at a wide field angle to image a diagnostic target and an index part for recognizing the position of the diagnostic target and by a narrow scan set at a field angle θ2 narrower than the field angle in the wide scan to image the diagnostic target with high time resolution. Then, the ultrasonic image (wide ultrasonic image) obtained by the wide scan is used to set spatial coordinates based on the index part. The spatial coordinates are used to align the ultrasonic image (narrow ultrasonic image) obtained by the narrow scan. Thus, the narrow ultrasonic image and the position of the diagnostic target included in the ultrasonic image (given ultrasonic image) corresponding to a given section in a volume can be objectively evaluated. For a more specific explanation, the example of the present embodiment is based on the following assumption: The heart of the fetus is targeted for a diagnosis. The spine is used as an index part to recognize the position of the heart. Moreover, for example, as shown in FIG. 2, two kinds of field angle settings including a wide scan (first scan) at a field angle θ1 and a narrow scan (second scan) at a field angle θ2 (note that θ1>θ2) are used. Nevertheless, this is merely illustrative, and the technical idea of the present invention is not restricted to the number of set field angles and the range of each field angle.

Figure 3:
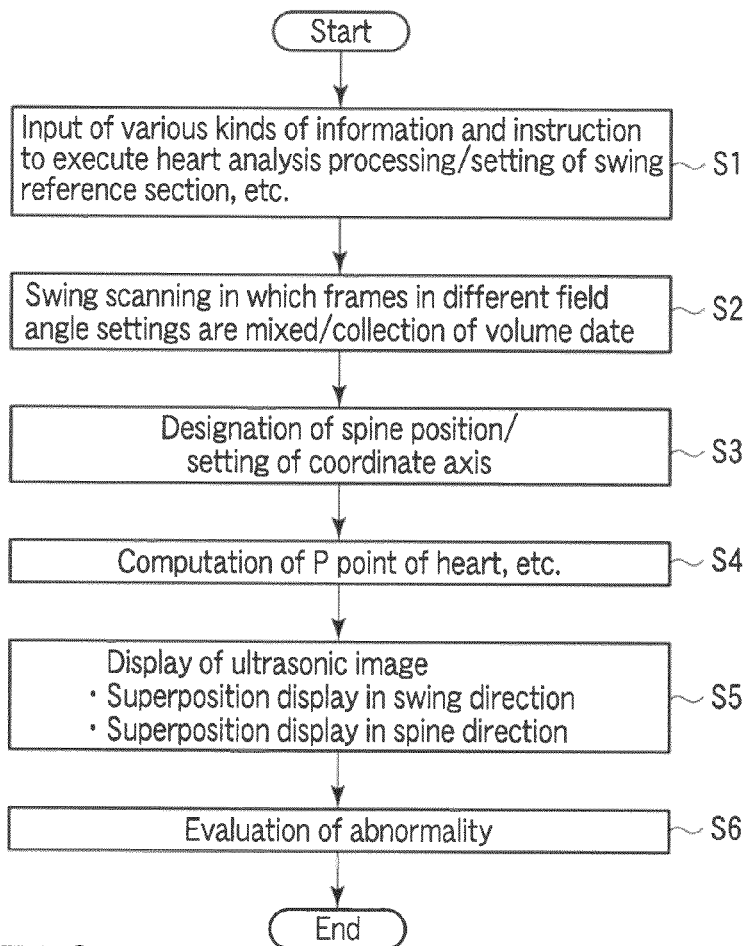
FIG. 3 is a flowchart showing the flow of processing (heart analysis processing) following the heart analysis function.

FIG. 3 is a flowchart showing the flow of processing (heart analysis processing) following the heart analysis function. The contents of the processing in each step shown in FIG. 3 are described below.

[Input of Various Kinds of Information and Instruction to Execute Heart Analysis Processing/Setting of Swing Reference Section, Etc.: Step S1]

First, various kinds of information such as patient information and an instruction to execute the heart analysis processing are input via the input unit 13, and a swing reference section, the field angle θ1 in the wide scan, the field angle θ2 in the narrow scan, an ROI (heart position), etc. are set (step S1).

Figure 4A:
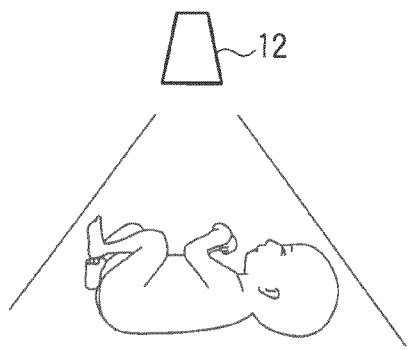
FIGS. 4A and 4B are diagrams for explaining the swing reference section setting in the case where the heart of a fetus is targeted for a diagnosis.
Figure 4B:
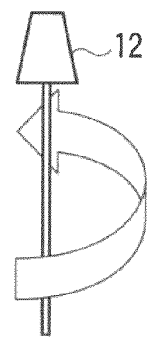
Figure 5A:
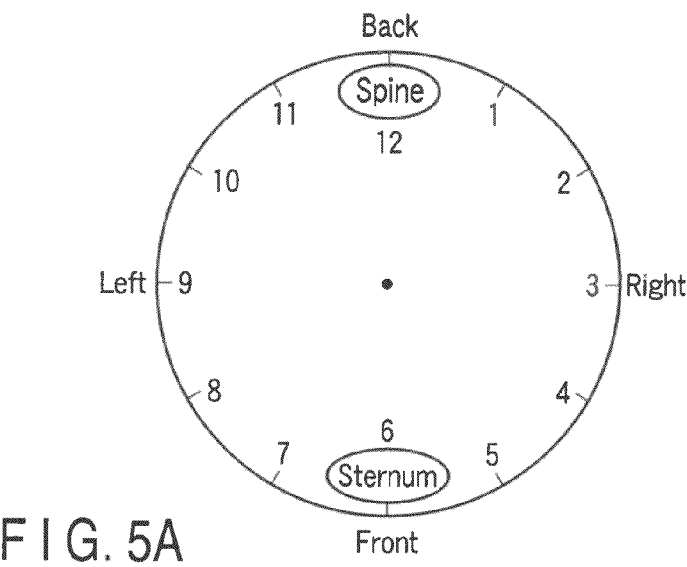
FIGS. 5A and 5B are diagrams for explaining the swing reference section setting in the case where the heart of the fetus is targeted for a diagnosis.
Figure 5B:
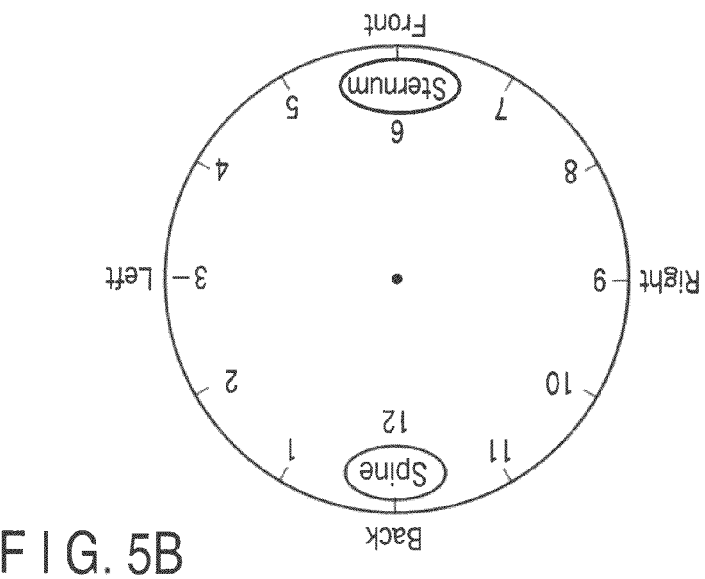

FIGS. 4, 5 and 6 are diagrams for explaining the swing reference section setting in the case where the heart of the fetus is targeted for a diagnosis. That is, as shown in FIG. 4A, the position of the ultrasonic probe 12 is set so that the head of the fetus appears in the right side of a screen. Thus, a fetus major axis tomogram is acquired. Then, as shown in FIG. 4B, if the ultrasonic probe 12 is rotated counterclockwise, three o'clock on the dial of the clock corresponds to the left direction of the fetus as shown in FIG. 5A when the ultrasonic probe 12 is viewed from above, so that the acquired ultrasonic tomogram is a chest minor axis tomogram. Suppose this chest minor axis tomogram turned upside down as shown in FIG. 5B. Then, as shown in FIGS. 6A and 6B, on the ultrasonic image, a point P (cardiac position) where the septum of the heart is in contact with the posterior wall of the atrium is located in the vicinity of the center, the heart is located in the vicinity of the upper left part, and the spine is located in the vicinity of the central lower part. A desired section is selected using an ultrasonic image that shows the heart, etc. in, for example, such a positional relation, and a predetermined operation for setting this section as a swing reference section is input via the input unit 13. Here, the swing reference section is, for example, a section located in the center of a swing range.

Then, on the image corresponding to the set swing reference section, ROIs in the wide scan and the narrow scan, the field angle θ1 in the wide scan and the field angle θ2 in the narrow scan are set by the operation from the input unit 13. That is, as shown in FIG. 7A, if a region which includes the spine serving as the basis for recognizing the diagnostic target heart and the position of the heart is set as an ROI on the swing reference section, a field angle for ultrasonically scanning the ROI is calculated in the control processor 28 and set as the field angle θ1. Moreover, as shown in FIG. 7B, if a region which includes the diagnostic target heart but does not include the spine is set as an ROI on the swing reference section, a field angle for ultrasonically scanning this ROI is computed in the control processor 28 and set as the field angle θ2. Further, the position on the body surface of the subject and the position of the spine are similarly set on the swing reference section.

In addition, in the present embodiment, when the field angle θ1 in the wide scan and the field angle θ2 in the narrow scan are set, a suitable volume rate (i.e., the number of wide scans and narrow scans performed per unit time) is calculated on the basis of each field angle in the control processor 28 and set as a scanning condition. However, the present invention is not restricted to this example, and a user may set a desired volume rate by manual setting within the range of the specification of the device. Moreover, in the example described above, the user manually sets the ROIs in the wide scan and the narrow scan in the swing reference section via the input unit 13. However, the present invention is not restricted to this example, and an ROI initially set in the device or an ROI set by an automatic setting function may be used for one of the ROIs (e.g., the ROI in the narrow scan). Properly, a user may set or change a position of ROI, a shape of ROI, a size of ROI and the like in the narrow scan. Typically, for example, a user may set or change a position of ROI, a shape of ROI and a size of ROI in the narrow scan by indicating the four vertexes of ROI shown in FIG. 7B via the input unit 13.

[Swing Scanning in which Frames in Different Field Angle Settings are Mixed/Collection of Volume Data: Step S2]

Then, the control processor 28 performs a volume scan by swinging including the wide scan and the narrow scan at different field angles θ1, θ2 in accordance with the swing reference section, the field angle, etc. set in step S1, thereby collecting volume data (step S2). This volume scan is performed for a predetermined period (e.g., a period equal to or more than at least one heartbeat), and time-series volume data corresponding to this period is acquired.

Figure 8A:
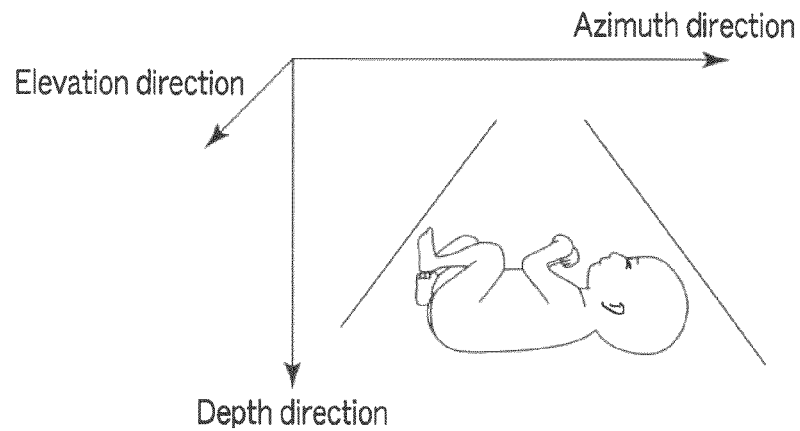
FIGS. 8A to 8C are diagrams for explaining a scan sequence in step S2.
Figure 8B:
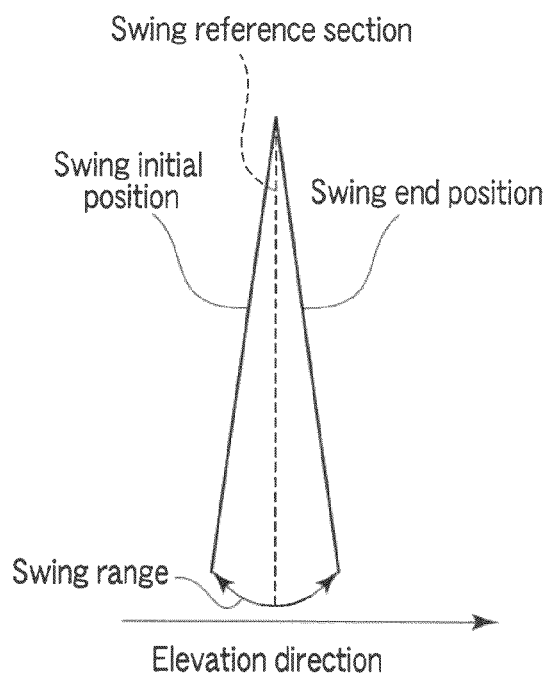
Figure 8C:
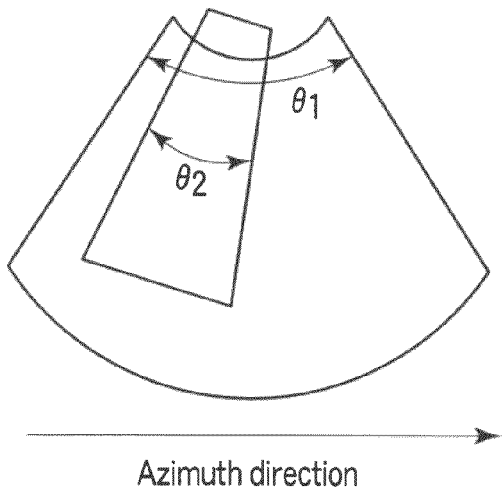

FIGS. 8A, B, C are diagrams for explaining the relation among the swing reference section, an ultrasonically scanned plane in the wide scan, an ultrasonically scanned plane in the narrow scan, and the swing range. As a result of the processing in step S1, the ultrasonic probe 12 is located in such a positional relation with the fetus as shown in FIG. 8A. The swing range in which the ultrasonically scanned plane swings has, as shown in, for example, FIG. 8B, an origin in a swing initial section along an elevation direction, an endpoint in a swing end section, and an intermediate point in the swing reference section. The control processor 28 swings the ultrasonically scanned plane (frame) in the swing range from the swing reference section to the swing initial section and the swing end section, thereby performing an ultrasonic scan in accordance with the wide scan or the narrow scan as shown in FIG. 8C.

Figure 9:
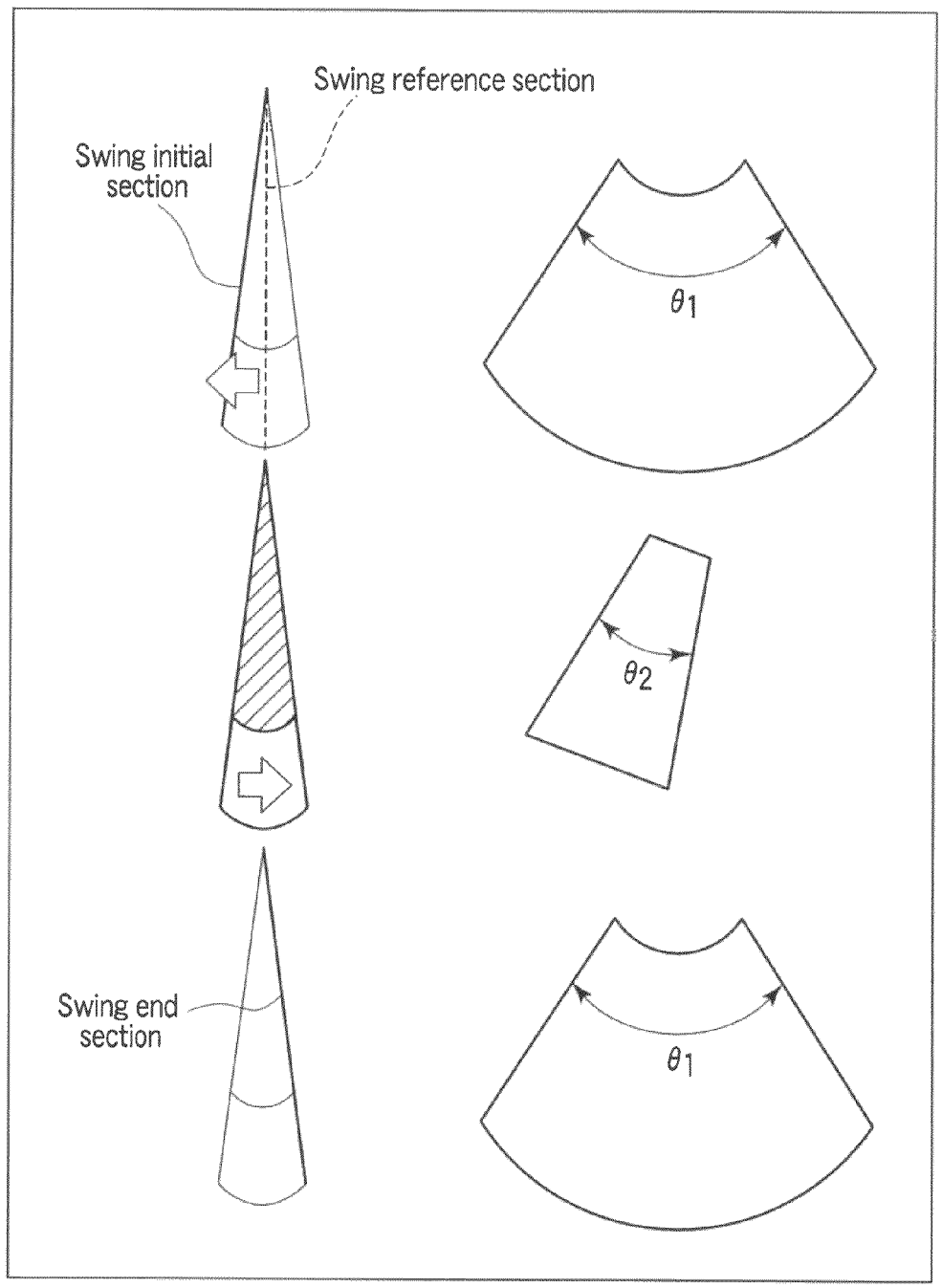
FIG. 9 is a diagram for explaining the scan sequence in step S2.

In addition, the position where the wide scan or the narrow scan is performed is not particularly limited in the elevation direction. The number of frames to be subjected to the wide scan is not particularly limited as long as it is within the range of an allowed volume rate (e.g., within the range that can maintain a certain degree of a real-time characteristic). In the present embodiment, in order to improve accuracy, the wide scan is performed in two places in the swing initial section and the swing end section, and the narrow scan is performed at other positions, for example, as shown in FIG. 9. In this case, in the swing range, an ultrasonic scan as shown in FIG. 10 is performed (each vertical segment corresponds to one frame).

[Designation of Spine Position/Setting of Coordinate Axis: Step S3]

Then, via the input unit 13, a spine position is designated on at least one ultrasonic image (e.g., an ultrasonic image corresponding to the swing initial section or an ultrasonic image corresponding to the swing end section) acquired by the wide scan, and a coordinate axis is set on the basis of the designated spine position (step S3).

That is, when, for example, the spine position can be determined on an ultrasonic image corresponding to the swing initial section, a spine position is designated via the input unit 13. When the spine position can not be determined on the ultrasonic image corresponding to the swing initial section, a spine position is designated on an ultrasonic image corresponding to the swing end section via the input unit 13. FIG. 11 illustrates the state of a spine position designated on the ultrasonic image corresponding to the swing initial section (or the ultrasonic image corresponding to the swing end section). The spine is not exclusively designated via the input unit 13. For example, the spine may be automatically designated by limiting to a particular region (in this case, a region corresponding to a deep part) on the ultrasonic image and extracting high luminance therefrom.

Figure 12:
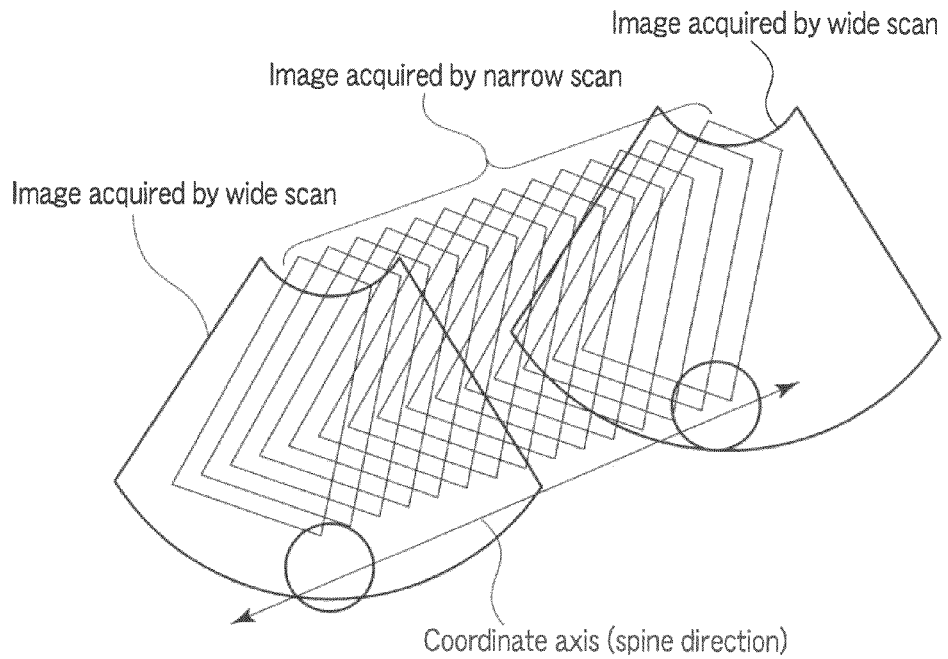
FIG. 12 is a diagram for explaining the setting of a coordinate axis using the spine as the a reference which is common to the wide ultrasonic images and narrow ultrasonic images.

Then, the control processor 28 finds, by a predetermined method such as a least squares method, a straight line (spine direction) passing the spine position on the ultrasonic image corresponding to the swing reference section designated in step S1 and the spine position designated in step S3, thereby setting a coordinate axis which is common to a plurality of ultrasonic images acquired by the wide scan and the narrow scan (i.e., ultrasonic images acquired by swinging), for example, as shown in FIG. 12. In addition, in the present embodiment, the spine direction is found by using two points including the spine position on the ultrasonic image corresponding to the swing reference section and the spine position on the ultrasonic image corresponding to the swing initial section (or on the ultrasonic image corresponding to the swing end section). However, the present invention is not limited thereto. For example, the spine direction may be defined by using the spine positions set on the ultrasonic images corresponding to the wide scan at three or more points including the swing reference section, the swing initial section and the swing end section.

[Computation of P Point of Heart, Etc.: Step S4]

Figure 13:
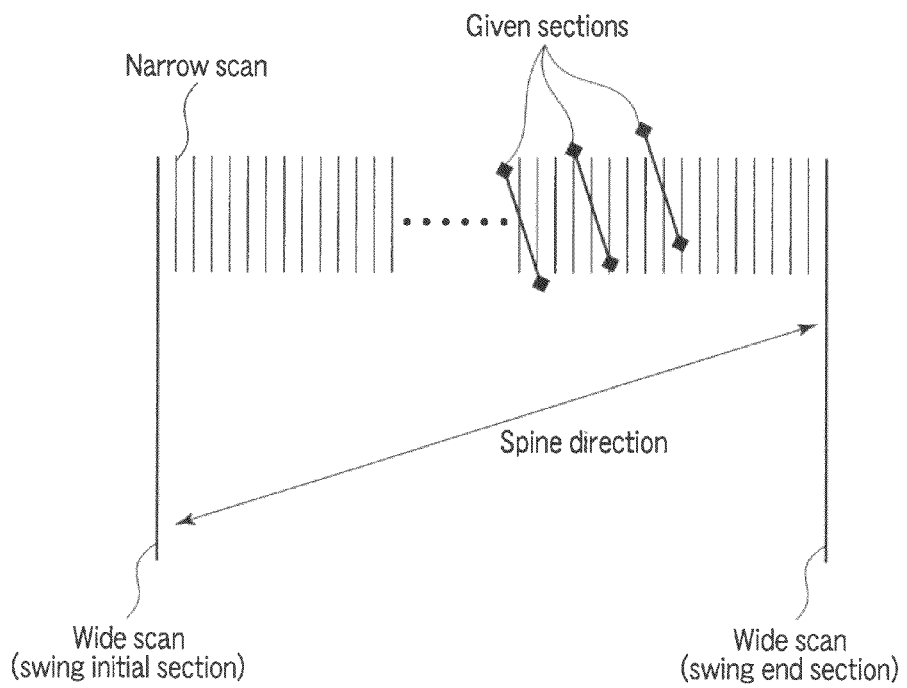
FIG. 13 is a diagram illustrating a plurality of given sections perpendicular to the spine direction set in volume data.

Then, the heart analysis unit 26 sets a plurality of given sections (e.g., given sectional positions perpendicular to the spine direction), for example, as shown in FIG. 13 on the basis of the spine direction set in step S3, and computes the position of a P point, the inclination of the septum, etc. using the ultrasonic image corresponding to the set given section (a given sectional ultrasonic image) (step S4).

FIG. 14 is a flowchart showing the flow of computing the P point of the heart, etc. according to step S4. As shown, first, the ultrasonic images of the plurality of given sections are reproduced in the form of moving images, and an ultrasonic image corresponding to the diastole of the heart (diastolic image) is designated via the input unit 13 (step S41).

Figure 16A:
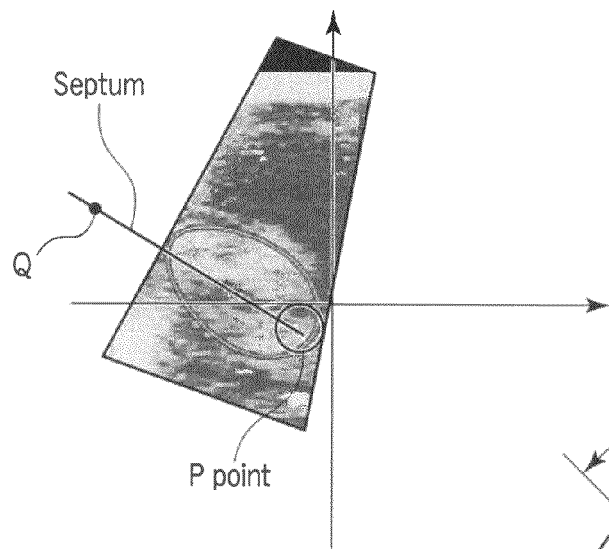
FIGS. 16A and 16B are diagrams for explaining the designation of a Q point on a septum and the computation of an inclination.
Figure 16B:
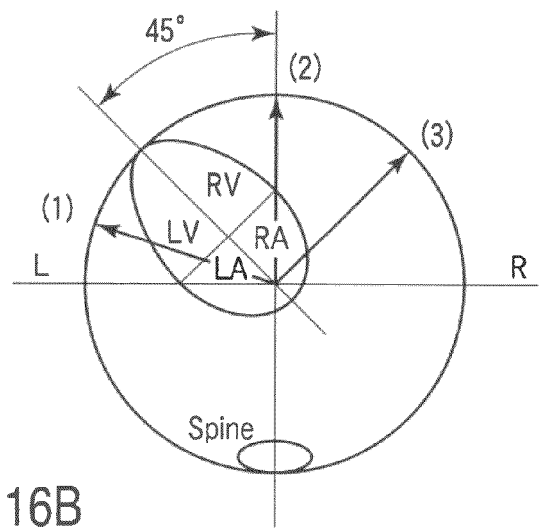

Then, when the position of the P point as shown in FIG. 15A is designated on the designated diastolic image via the input unit 13, the heart analysis unit 26 computes, as shown in FIG. 15B, the position (coordinates) of the P point based on the coordinate axis set in step S3 (step S42). Further, when a desired point (Q point) on the septum as shown in FIG. 16A is designated on the designated diastolic image via the input unit 13, the heart analysis unit 26 computes, as shown in FIG. 16B, the position (coordinates) of the designated Q point on the septum, and also computes the inclination of the septum from the P point and the Q point on the septum (step S43). From the position of the P point, the inclination of the septum, etc. that have been obtained, the heart analysis unit 26 creates a predetermined score for evaluating the abnormality of the heart (step S44).

[Display of Ultrasonic Image: Step S5]

Then, in the present embodiment, the control processor 28 controls the monitor 14 and others so that the wide ultrasonic image, the narrow ultrasonic image and the given section ultrasonic image are displayed in a predetermined form (step S6). Specific display forms are described below in accordance with Examples. Note that, the display form described in the present embodiment is not limited to examples as the following. An user may use any display form in such a manner that at least two of the wide ultrasonic image, the narrow ultrasonic image, the given section ultrasonic image, the coordinate and the position according to the coordinate.

Example 1

Figure 17:
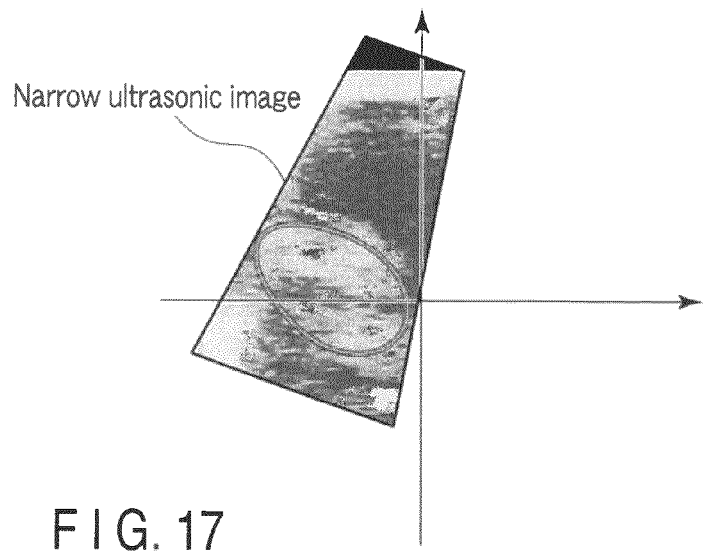
FIG. 17 is a diagram showing one example of a display form of the narrow ultrasonic image acquired by the heart analysis function.

The wide ultrasonic image, the narrow ultrasonic image and the given section ultrasonic image can be displayed independently or side by side. Here, as shown in FIG. 17, each ultrasonic image is displayed so that a coordinate axis based on the spine position is set therein. Such a display form makes it possible to objectively evaluate the positional relation between the heart and the spine.

Example 2

The wide ultrasonic image and the narrow ultrasonic image can be displayed in such a manner as to be superposed on each other along the swing direction. That is, a coordinate axis based on the spine position is set on the wide ultrasonic image (e.g., on the ultrasonic image corresponding to the swing initial section) and displayed. This coordinate axis is a vertical straight line whose vertical axis includes the spine position and whose horizontal axis is located between the spine position and the body surface set in step S1. The narrow ultrasonic image including the heart is superposed on the wide ultrasonic image, and these images are displayed in such a manner as to maintain a proper positional relation. Here, the coordinate axis based on the spine position may not be displayed as shown in FIG. 18A or may be displayed as shown in FIG. 18B. Such a display form makes it possible to display the wide ultrasonic image and the narrow ultrasonic image in a proper positional relation based on the spine and to objectively evaluate the positional relation between the heart and the spine.

Example 3

The wide ultrasonic image and the given section ultrasonic image can be displayed in such a manner as to be superposed on each other along the direction of the spine. That is, a coordinate axis based on the spine position is set on the wide ultrasonic image (e.g., on the ultrasonic image corresponding to the swing initial section) and displayed, as in Example 2. The given section ultrasonic image including the heart is superposed on the wide ultrasonic image, and these images are displayed in such a manner as to maintain a proper positional relation. Here, the display of the coordinate axis based on the spine position can be controlled as in Example 2. Such a display form makes it possible to display the wide ultrasonic image and the given section ultrasonic image in a proper positional relation based on the spine and to objectively evaluate the positional relation between the heart and the spine.

Example 4

When the superposition display in Example 3 or Example 4 is performed, the wide ultrasonic image, the narrow ultrasonic image and the given section ultrasonic image can be displayed in different colors respectively assigned thereto. For example, when the narrow ultrasonic image (or the given section ultrasonic image) is displayed in such a manner as to be superposed on the wide ultrasonic image, the narrow ultrasonic image (or the given section ultrasonic image) is displayed as a color image, and the region of the wide ultrasonic image on which the narrow ultrasonic image is not superposed is displayed in a monotone state. Alternatively, a predetermined color is assigned to the borderline of the narrow ultrasonic image or the given section ultrasonic image, so that the borderline between the narrow ultrasonic image or the given section ultrasonic image and the wide ultrasonic image is displayed in a clear state. Such display makes it possible for the user to visually recognize, easily and quickly, the borderline between the narrow ultrasonic image or the given section ultrasonic image and the wide ultrasonic image and the range of the narrow ultrasonic image or the given section ultrasonic image on the wide ultrasonic image.

[Evaluation of Abnormality: Step S6]

Then, the heart analysis unit 26 evaluates an abnormality of the position of the heart, etc. using the score created in step S4 (step S6). The result of the evaluation is displayed on the monitor 14 in a predetermined form together with the ultrasonic image or independently.

(Effects)

The following effects can be obtained according to the configuration described above.

According to the present ultrasonic diagnostic apparatus, volume data are collected by the swing scanning in which the frames in different field angle settings are mixed by the wide scan set at a wide field angle to image a diagnostic target and an index part for recognizing the position of the diagnostic target and by the narrow scan set at a field angle $\theta 2$ narrower than the field angle in the wide scan to image the diagnostic target with high time resolution. Then, the wide ultrasonic image is used to set spatial coordinates based on the index part. The spatial coordinates are used to align the narrow ultrasonic image. While this positional relation is being maintained, the wide ultrasonic image, the narrow ultrasonic image and the given section ultrasonic image are displayed in a predetermined form. Thus, without substantially decreasing the volume rate, the position of the heart imaged in the narrow ultrasonic image and the given section ultrasonic image can be objectively and accurately recognized on the basis of the position of the spine.

Furthermore, according to the present ultrasonic diagnostic apparatus, the position of the P point, the inclination of the septum, etc. are computed using the aligned narrow ultrasonic image and the given section ultrasonic image, and are used to evaluate the abnormality of the heart. Thus, the abnormality of the heart can be objectively and accurately evaluated.

Still further, according to the present ultrasonic diagnostic apparatus, the wide ultrasonic image, the narrow ultrasonic image and the given section ultrasonic image can be displayed independently or displayed simultaneously so that the positional relation is maintained on the coordinate axis based on the spine. The operator can observe the aligned wide ultrasonic image, narrow ultrasonic image and given section ultrasonic image in various forms by selecting a given display form, so that the degree of freedom in an image diagnosis can be increased.

It is to be noted that the present invention is not exclusively limited to the embodiment described above, and the components can be modified at the stage of carrying out the invention without departing from the sprit thereof. There are, for example, specific modifications as below.

(1) The functions according to the present embodiment can be achieved by installing programs for performing the processing of the functions on a computer in, for example, a workstation, and expanding the programs on a memory. In this case, the program that can cause the computer to perform this procedure can be distributed in such a manner as to be stored in a recording medium such as a magnetic disk (e.g., a floppy (registered trademark) disk, a hard disk), an optical disk (e.g., a CD-ROM, a DVD) or a semiconductor memory.

(2) In the configuration described in the embodiment, an analysis of, for example, the heart is performed using an ultrasonic image output from the image generating unit 25 (i.e., the ultrasonic image after scan conversion). However, the target ultrasonic image data is not limited to the ultrasonic image after the scan conversion, and may be raw data before the scan conversion. In such a case, the magnitude of a signal value is used instead of a luminance value, so that the same effects can be obtained.

(3) In the case described in the embodiment, volume data are collected by the swing scanning in which the frames in different field angle settings are mixed by the wide scan (first scan) at a field angle θ and the narrow scan (second scan) at a field angle θ2 (θ1>θ2). However, the technical idea of the present invention is not restricted to this example. For example, the wide scan and the narrow scan may be performed for substantially the same section, and two-dimensional scans in different field angle settings may be repeated. According to such a configuration, the narrow scan can be selectively performed for a particular region (e.g., an ROI including the diagnostic target). As a result, the ultrasonic scan of the region of interest can be performed at a high rate, and an ultrasonic image with high time resolution can be acquired.

(4) The scan line density in the narrow scan at a field angle θ2 (θ1>θ2) can be higher than the scan line density in the wide scan at a field angle θ1. For example, when the number of scan lines in the narrow scan is about the same as the number of scan lines in the wide scan, the spatial resolution (bearing resolution) of the narrow scan in which the diagnostic target is a scanned region can be θ1/θ2 times that in the wide scan. In addition, the scan line density in the narrow scan at a field angle θ2 can be lower than the scan line density in the wide scan at a field angle θ1. The change of the scan line density can be performed by inputting the instruction of the change via the input unit 13.

(5) The azimuth resolution of the wide scan be controlled by controlling the number of execution of the wide scan. For example, the azimuth resolution may be enhanced by executing a wide scan only once instead of executing it an n number of times (n: an integer larger than 1) in such a manner that the scan line density in that one-time wide scan is high (e.g. a scan line density that is three times as high as the normal scan line density). On the other hand, the azimuth resolution may be reduced by executing a wide scan an n number of times instead of executing it once.

(6) The transmission/reception conditions and the image quality conditions can be set independently and respectively. For example, the gain of the wide scan may be different from the gain of the narrow scan.

Various inventions can be formed by suitable combinations of a plurality of components disclosed in the embodiment described above. For example, some of all the components shown in the embodiment may be eliminated. Moreover, the components in different embodiments may be suitably combined together.

What is claimed is:

1. An ultrasonic diagnostic apparatus, comprising:
an ultrasonic probe which acquires ultrasonic image data by performing a first ultrasonic scan and a second ultrasonic scan in a scan plane set in a subject, the first ultrasonic scan using a first field angle set to a size including a diagnostic target and a part serving as an index to recognize a position of the diagnostic target, and the second ultrasonic scan including the diagnostic target in the subject, wherein the second ultrasonic scan has a field angle smaller than a field angle of the first ultrasonic scan;
a control processor which controls the ultrasonic probe to perform a sequence of scans so that a plurality of ultrasonic image data sets regarding the diagnostic target are acquired by selectively performing both a second plurality of second ultrasonic scans and a first plurality of first ultrasonic scans in the sequence, wherein the control processor controls the ultrasonic probe to perform more second ultrasonic scans than first ultrasonic scans; and
user interface hardware which sets, in the ultrasonic image data, a coordinate axis based on the index part by use of a second ultrasonic image obtained by the second ultrasonic scan.

2. The ultrasonic diagnostic apparatus according to claim 1, further comprising a display which displays the coordinate axis so that the coordinate axis is superposed on one of the second ultrasonic image, a first ultrasonic image acquired by the first ultrasonic scan, and an ultrasonic image corresponding to a given section set in the plurality of ultrasonic image data sets.

3. The ultrasonic diagnostic apparatus according to claim 1, further comprising a display which displays a first ultrasonic image obtained by the first ultrasonic scan or an ultrasonic image corresponding to a given section set in the plurality of ultrasonic image data sets so that this image is superposed on a corresponding position on the second ultrasonic image.

4. The ultrasonic diagnostic apparatus according to claim 2, further comprising a display which displays a first ultrasonic image obtained by the first ultrasonic scan or an ultrasonic image corresponding to a given section set in the plurality of ultrasonic image data sets so that this image is superposed on a corresponding position on the second ultrasonic image.

5. The ultrasonic diagnostic apparatus according to claim 2, wherein the display displays one of the first ultrasonic image and the second ultrasonic image in a color different from that of the other when the first ultrasonic image and the second ultrasonic image are superposed.

6. The ultrasonic diagnostic apparatus according to claim 2, wherein the display displays a borderline between the first ultrasonic image and the second ultrasonic image when the first ultrasonic image and the second ultrasonic image are superposed.

7. The ultrasonic diagnostic apparatus according to claim 1, further comprising a processor which evaluates at least one of a position, size, shape, and structure of the diagnostic target by use of the ultrasonic image data in which the coordinate axis is set.

8. The ultrasonic diagnostic apparatus according to claim 1, wherein the control processor controls the ultrasonic probe so that volume data for an ultrasonic image of the diagnostic target is acquired by mechanically swinging a scan plane in the first ultrasonic scan and a scan plane in the second ultrasonic scan and simultaneously performing at least one first ultrasonic scan and the second plurality of second ultrasonic scans.

9. The ultrasonic diagnostic apparatus according to claim 1, wherein the control processor controls the ultrasonic probe so that the first ultrasonic scan is performed in at least one of a section at an initial position of a swing, a section at an end position of the swing and a given section between the initial position and the end position.

10. The ultrasonic diagnostic apparatus according to claim 1, wherein the control processor controls the ultrasonic probe so that volume data for an ultrasonic image of the diagnostic target is acquired by electronically swinging a scan plane in the first ultrasonic scan and a scan plane in the second ultrasonic scan and simultaneously performing at least one first ultrasonic scan and the second plurality of second ultrasonic scans.

11. The ultrasonic diagnostic apparatus according to claim 1, wherein the control processor performs at least one first ultrasonic scan and the second plurality of second ultrasonic scans in substantially a same scan plane.

12. The ultrasonic diagnostic apparatus according to claim 1, wherein the user interface hardware changes a transmission/reception condition including at least one of a density and a gain of an ultrasonic transmission beam in the second ultrasonic scan, and wherein the control processor controls the changed transmission/reception condition in the second ultrasonic scan.

13. The ultrasonic diagnostic apparatus according to claim 1, wherein the user interface hardware sets the coordinate axis by use of at least one of the initially set index part and the second ultrasonic image.

14. The ultrasonic diagnostic apparatus according to claim 1, wherein the subject is a fetus,
the diagnostic target is a heart, and
the index part is a spine.

15. The ultrasonic diagnostic apparatus according to claim 1, wherein the user interface hardware inputs at least one of a shape and size of a region scanned by the first ultrasonic scan.

16. The ultrasonic diagnostic apparatus according to claim 15, wherein the user interface hardware inputs at least one of the shape and size of the scanned region in a scan plane corresponding to an initial time phase of the first ultrasonic scan or the second ultrasonic scan.

17. An ultrasonic image processing apparatus, comprising:
a non-transitory memory which stores a plurality of ultrasonic image data sets, the ultrasonic image data sets being acquired by performing a first ultrasonic scan and a second ultrasonic scan in a scan plane set in a subject, the first ultrasonic scan using a first field angle set to a size including a diagnostic target and a part serving as an index to recognize a position of the diagnostic target, and the second ultrasonic scan using a second field angle set to a size including the diagnostic target in the subject, wherein the second ultrasonic scan has a field angle smaller than a field angle of the first ultrasonic scan, and the plurality of ultrasonic image data sets are obtained by selectively performing both a second plurality of second ultrasonic scans and a first plurality of first ultrasonic scans in a sequence, so that more second ultrasonic scans are performed than first ultrasonic scans; and
user interface hardware which sets, in the plurality of ultrasonic image data sets, a coordinate axis based on the index part by use of at least one of second ultrasonic images obtained by the second ultrasonic scan.

18. An ultrasonic image acquiring method, comprising:
acquiring a plurality of ultrasonic image data sets regarding a diagnostic target by performing a first ultrasonic scan and a second ultrasonic scan in a scan plane set in a subject, the first ultrasonic scan using a first field angle set to a size including a diagnostic target and a part serving as an index to recognize the position of the diagnostic target and the second ultrasonic scan using a second field angle set to a size including the diagnostic target in the subject, wherein the second ultrasonic scan has a field angle smaller than a field angle of the first ultrasonic scan, and the plurality of ultrasonic image data sets are obtained by causing, by a control processor, an ultrasonic probe to perform a sequence of scans, including selectively performing both a second plurality of second ultrasonic scans and a first plurality of first ultrasonic scans in the sequence, so that more second ultrasonic scans are performed than first ultrasonic scans; and
setting, in the ultrasonic image data, a coordinate axis based on the index part by use of at least one of second ultrasonic images obtained by the second ultrasonic scan.

19. An ultrasonic image display method, comprising:
setting a coordinate axis based on an index part in a plurality of ultrasonic image data sets, the plurality of ultrasonic image data sets being obtained by performing a first ultrasonic scan and a second ultrasonic scan in a scan plane set in a subject, the first ultrasonic scan using a first field angle set to a size including a diagnostic target and a part serving as an index to recognize the position of the diagnostic target and the second ultrasonic scan using a second field angle set to a size including the diagnostic target in the subject, wherein the second ultrasonic scan has a field angle smaller than a field angle of the first ultrasonic scan, and the plurality of ultrasonic image data sets are obtained by causing, by a control processor, an ultrasonic probe to perform a sequence of scans, including selectively performing both a second plurality of second ultrasonic scans and a first plurality of first ultrasonic scans in the sequence, so that more second ultrasonic scans are performed than first ultrasonic scans; and displaying a superposed image on which at least two of the coordinate axis, a position according to the coordinate axis, the first ultrasonic image, a second ultrasonic image acquired by the second ultrasonic scan, and an ultrasonic image corresponding to a given section set in the plurality of ultrasonic image data sets are superposed.

* * * * *